United States Patent [19]

Fuchs et al.

[11] Patent Number: 5,087,760
[45] Date of Patent: Feb. 11, 1992

[54] PROCESS FOR THE PRODUCTION OF 1,3-CYCLOPENTANEDIONE

[75] Inventors: Rudolf Fuchs, Sion; John McGarrity, Visp, both of Switzerland

[73] Assignee: Lonza Ltd., Basle, Switzerland

[21] Appl. No.: 460,658

[22] Filed: Jan. 3, 1990

[30] Foreign Application Priority Data

Jan. 6, 1989 [CH] Switzerland ............... 00041/89

[51] Int. Cl.$^5$ ............................................. C07C 45/00
[52] U.S. Cl. .................................. 568/361; 560/181; 560/121
[58] Field of Search ............................ 568/361, 379

[56] References Cited

U.S. PATENT DOCUMENTS

| | | | |
|---|---|---|---|
| 3,518,296 | 6/1970 | Bucourt | 568/379 |
| 3,531,504 | 9/1970 | Coria | 568/379 |
| 3,931,322 | 1/1976 | Hengartner | 568/379 |
| 4,132,726 | 1/1979 | Kurozumi et al. | 568/361 |
| 4,168,280 | 9/1979 | Nash | 568/379 |
| 4,892,966 | 1/1990 | Wild | 568/379 |

FOREIGN PATENT DOCUMENTS 1230022 12/1966 Fed. Rep. of Germany.
1404429 12/1963 France.
4047745 12/1974 Japan.

OTHER PUBLICATIONS

Chemical Abstracts, Vol. 107, par. 197620j (1987).
Aldrichimica Acta, Vol. 10, Nov. 1, 1977, p. 19.
Carlo Lick and Kurt Schank, 1,3-Cyclopentanedione-a Prized Reagent, Chemische Berichte, Vol. III, (1978, pp. 2461-1464).

*Primary Examiner*—Paul J. Killos
*Attorney, Agent, or Firm*—Fisher, Christen & Sabol

[57] ABSTRACT

A process for the production of 1,3-cyclopentanedione, which is a versatile intermediate product for numerous active ingredient syntheses. For this purpose, a malonic acid ester is reacted with a haloalkoxybutenoic acid ester, the resultant bis-(alkoxycarbonyl) alkoxypentenoic acid ester is cyclized to alkoxycarbonyl alkoxycyclopentenone, the ester function is saponified, and finally the intermediate is decarboxylated to the end product.

15 Claims, No Drawings

PROCESS FOR THE PRODUCTION OF 1,3-CYCLOPENTANEDIONE

BACKGROUND OF THE INVENTION

1. Field of the Invention

The invention relates to the production of 1,3-cyclopentanedione.

2. Background of the Art 1,3-Cyclopentanedione or its derivatives are interesting intermediate products for numerous active ingredient syntheses, e.g., according to Chemical Abstracts, 107:197620 it is useful as the starting product for the production of a prostaglandin intermediate product or according to Tetrahedron Letters, Vol. 22, No. 44, (1981), p. 4385ff, as base substances for the antibiotic Kjellmanianone. Other uses are listed in Aldrichimica Acta, Vol. 10, No. 1, (1977), p. 19.

The known processes for the production of 1,3-cyclopentanedione are just as numerous.

According to widespread synthesis methods, 1,3-cyclopentadiene is used as the starting product, which is converted into 1,3-cyclopentenediol, by oxidation into 1,3-cyclopentenedione and, after final hydrogenation, into 1,3-cyclopentanedione. As described by Lick et al. in Chem. Ber., 111, (1978), p. 2466, these methods are connected with numerous difficulties and are not very successful in the production of considerable amounts of product. The same authors have developed a process of their own in which 2-norbornene is converted into 1,3-cyclopentanedione in a three-step synthesis with a 70 percent yield [Chem. Ber., 111, (1978), p. 2461f].

By the necessary ozonolysis at −60° to −70° C., required twice in the process, the process because of the energy expenditure (cooling, ozone production) is not very profitable for conversion into an industrial process.

BROAD DESCRIPTION OF THE INVENTION

The object of the invention is to provide a process for the production of 1,3-cyclopentanedione that does not exhibit the above-mentioned drawbacks.

It has been found that the object of the invention can be attained in a surprisingly good way by means of the invention process. The invention involves a process for the production of 1,3-cyclopentanedione. In a first step (a) of the invention process, a malonic acid ester in the presence of a base is reacted with a 4-halo-3-alkoxy-2E-butenoic acid ester to a 5,5-bis-(alkoxycarbonyl)-3-alkoxy-2E-pentenoic acid ester of the formula:

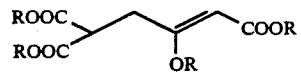

wherein the radicals R are each the same or different and are an alkyl having 1° to 4° C. atoms. In the second step (b), the pentenoic acid ester is cyclized in the presence of a base to the corresponding salt of 5-alkoxycarbonyl-3-alkoxy-2-cyclopenten-1-one of the formula:

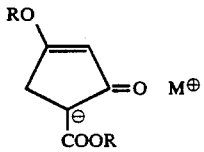

wherein M is sodium or potassium and R has the above-named meaning. In step (c), the ester function is saponified in the presence of a base. Finally, in step (d), the cyclic compound is decarboxylated in the presence of a mineral acid to the end product.

Decisive for the economy of the invention process is the fact that one can start from commercially-available malonic acid esters and 4-halo-3-alkoxy-2E-butenoic acid esters which are easily available from diketene or 4-haloacetic acid esters.

The invention also includes the 5,5-bis-(alkoxycarbonyl)-3-alkoxy-2E-pentenoic acid esters of the formula:

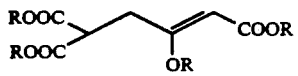

wherein the Rs are the same or different and are alkyl having 1° to 4° C. atoms. Preferably the pentenoic acid is 5,5-bis-(ethoxycarbonyl)-3-methoxy-2E-pentenoic acid methyl ester, or 5,5-bis-(methoxycarbonyl)-3-methoxy-2E-pentenoic acid methyl ester, or 5,5-bis-(ethoxycarbonyl)-3-ethoxy-2E-pentenoic acid ethyl ester.

DETAILED DESCRIPTION OF THE INVENTION

Step (a)

According to the invention process, in a first step, a malonic acid ester in the presence of a base is reacted with a 4-halo-3-alkoxy-2E-butenoic acid ester to the corresponding 5,5-bis-(alkoxycarbonyl)-3-alkoxy-2E-pentenoic acid ester. Suitably the malonic acid di-($C_1$–$C_4$)-alkyl ester, preferably the malonic acid di-($C_1$–$C_2$)-alkyl ester, is used. The 4-halo3-alkoxy-2E-butenoic acid-($C_1$–$C_4$considered as suitable derivatives of the 4-halo-3-alkoxy-2E-butenoic acid esters; the 4-chloro-3-($C_1$–$C_2$)-alkoxy-2E-butenoic acid-($C_1$–$C_2$)-alkyl esters are especially suitable.

Alkali alcoholates, alkali hydroxides or strong organic bases, preferably alkali alcoholates, are used as the base. The term alkali alcoholate is understood to mean sodium or potassium alcoholates of lower aliphatic, optionally-branched, alcohols, such as, methanol, ethanol, propanol or butanol. Suitable representatives of the alkali hydroxides are potassium hydroxide or sodium hydroxide; and DBU [1,8-diazabicyclo(5,4,0)-undec-7-ene]can be used as the strong organic base. Suitably the reaction takes place in the presence of a polar solvent from the series acetonitrile, benzonitrile, lower aliphatic alcohols, such as, methanol or ethanol, 1,2-dimethoxyethane, N,N'-dimethylformamide or N,N'-dimethylacetamide. N,N'-dimethylformamide is the preferred solvent. The reaction temperature is advantageously selected between 0° and 180° C. and is especially preferred between 20° and 60° C.

The previously unknown 5,5-bis-(alkoxycarbonyl)-3-alkoxy-2E-pentenoic acid esters of the formula:

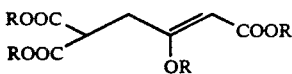

are obtained as the reaction product. The radicals R, which correspond to the ester groups or alkoxy groups of the malonic acid esters or 4-halo-3-alkoxy-2E-butenoic acid esters which are used, are the same or different and are alkyl having 1 to 4° C atoms. The 5,5-bis-[($C_1$–$C_2$)-alkoxycarbonyl]-3($C_1$–$C_2$)-alkoxy-2E-pentenoic acid-($C_1$–$C_2$)-alkyl esters are especially advantageous for the synthesis of 1,3-cyclopentanedione. Such compounds can be isolated in the usual way but as a rule are used directly in the following step (b) without special preparation.

Step (b)

Step (b) comprises the ring closure of the 5,5-bis-(alkoxycarbonyl)-3-alkoxy-2E-pentenoic acid esters in the presence of a base. The sodium or potassium alcoholates of the lower aliphatic alcohols methanol, ethanol, propanol or butanol or the alkali hydroxides potassium hydroxide or sodium hydroxide corresponding to step (a) are used as the base. As a rule the alcohol corresponding to the alcoholate is the solvent for the ring closure. But other polar solvents, such as, acetonitrile or benzonitrile, can be used. The ring closure suitably takes place at temperatures between 0° and 180° C., preferably between 20° and 60° C.

The corresponding salt of 5-alkoxycarbonyl-3-alkoxy-2-cyclopenten-1-one of the formula:

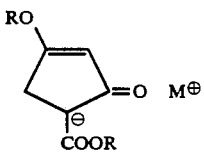

wherein M is sodium or potassium and R has the above-mentioned meaning, is obtained as the reaction product.

Steps (c) and (d)

To obtain 1,3-cyclopentanedione, the ester group of the salt of step (b) is saponified (step c) and the carboxyl group is finally decarboxylated.

Suitable bases for the saponification are aqueous solutions of sodium hydroxide or potassium hydroxide. The saponification temperature is advantageously between 0° and 100°, preferably room temperature.

The resultant carboxylic acid salt as a rule is not isolated but is further treated in situ with another acid. Suitable acids are the inorganic mineral acids, such as, hydrochloric acid or sulfuric acid.

The decarboxylation and, therefore, the conversion into 1,3-cyclopentanedione goes along with the acid treatment, which suitably takes place at temperatures between 20° and 100° C.

After the usual working up, the desired product can be obtained in good quality and good yields.

The following examples disclose the process according to the invention in more detail.

EXAMPLE 1

(a) Production of 5,5-bis-(ethoxycarbonyl)-3-methoxy-2E-pentenoic acid methyl ester 83.9 g (0.5 mol) of malonic acid diethyl ester was placed in 250 ml of N,N'-dimethylformamide. 27.8 g (0.5 mol) of sodium methylate was added at 20° C.; 10 minutes later 41.6 g (0.25 mol) of 4-chloro-3-methoxy-2E-butenoic acid methyl ester was added within 5 minutes. It was stirred for 2 hours at 20° C. Then 10.8 g (0.2 mol) of sodium methylate was added once more. After stirring for 15 hours at 20° C., N,N'-dimethylformamide was distilled off at 40° to 50° C./20 mbars. 120 ml of water and 100 ml of methylene chloride were added to the residue. After neutralization of the phases, the organic phase was separated and evaporated to dryness. The residue was distilled in a vacuum at 176° to 180° C./20 mbars. 58.8 g (80 percent) of the compound, with a purity of 98 percent (GC), was obtained. Data for the title compound was:

$^1$H-NMR: (CDCl$_3$, 300 MHz) δ
1.25, t J=6 Hz, 6H
3.4, d J=8 Hz, 2H
3.6, s, 3H
3.68, s, 3H
3.71, t J=8 Hz, 1H
4.16, q J=6 Hz, 4H
5.06, s, 1H (a1) Production of 5,5-bis(methoxycarbonyl)-3-methoxy-2E-pentenoic acid methyl ester 66 g (0.5 mol) of malonic acid dimethyl ester was placed in 250 ml of N,N'-dimethylformamide. 27.8 g (0.5 mol) of sodium methylate was added at 20°C.; 10 minutes later 41.6 g (0.25 mol) of 4-chloro-3-methoxy-2E-butenoic acid methyl ester was added within 5 minutes. It was stirred for 2 hours at 20° C. Then 10.8 g (0.2 mol) of sodium methylate was added once more. After stirring for 15 hours at 20° C. it was distilled off. After working up according to Example (a) 53.8 g (81 percent) of the title compound, with a purity of 98 percent (GC), was obtained. Data for the title compound was:

$^1$H-NMR: (CDCl$_3$, 300 MHz) δ
3.4, d, J=8 Hz, 2H
3.60, s, 3H
3.66, s, 3H
3.71, s, 6H
3.7, t, J=8 Hz, 1H
5.1, s, 1H (a2) Production of 5,5-bis-(ethoxycarbonyl)-3-methoxy-2E-pentenoic acid methyl ester 83.9 g (0.5 mol) of malonic acid diethyl ester was placed in 250 ml of N,N'-dimethylformamide. 27.8 g (0.5 mol) of sodium methylate was added at 20° C., 10 minutes later 48 g (0.25 mol) of 4-chloro-3-ethoxy-2E-butenoic acid methyl ester was added within 5 minutes. It was stirred for 2 hours at 20° C. Then 10.8 g (0.2 mol) of sodium methylate was added once more. After stirring for 15 hours at 20° C., the solvent was distilled off. After working up according to Example (a), 63.75 g (79 percent) of the title compound, with a purity of 98 percent (GC), was obtained. Data for the compound was:

$^1$H-NMR: (CDCl$_3$, 300 MHz) δ
1.2–1.35, m, 12H
3.41, d, J=8 Hz, 2H
3.71, t, J=8Hz, lH
3.80, q, J=8Hz, 2H
4.1–4.18, m, 6H
5.02, s, lH (b) Production of 5-ethoxycarbonyl-3-methoxy-2-cyclopenten-1-one 9 g (56 mmol) of malonic acid diethyl ester was placed in 50 ml of N,N'-dimethylformamide. 3 g (56 mmol) of sodium methylate Was added at 20° C.; 10 minutes later 8.25 g (50 mmol) of 4-chloro-3-methoxy-2E-butenoic acid methyl ester was added within 5 minutes. It was stirred for 1.5 hours at 20° C., after further addition of 0.9 g (17 mmol) of sodium methylate, it was stirred for 1.5 hours more. Then the N,N'-dimethylformamide was distilled off at 40° to 50° C./20 mbars. 100 ml of water and 100 ml of methylene chloride were added to the residue. The organic phase was separated and the aqueous phase was extracted with 80 ml of methylene chloride. The combined organic phases were concentrated by evaporation and the residue was dissolved in 100 ml of ethanol. 3.5 g (51 mmol) of sodium methylate, dissolved in 100 ml of ethanol, was added to this solution during 15 minutes at 20° C. The title compound precipitated out after 2 hours with stirring at 60° C. Then 100 ml of toluene was instilled at 60° C. and cooled to 0° C. 5.43 g (52.5 percent) of the title compound was obtained after filtering and drying. Data for the title compound was:

$^1$H-NMR: (CDCl$_3$, 300 MHz) δ
1.30, t, J=7.5 Hz, 3H
2.79, dd, J1=18 Hz, J2=7.5 Hz, lH
3.06, dd, J1=18 Hz, J3=3 Hz, lH
3.52, dd, J2=7.5 Hz, J3=3 Hz, lH
3.89, s, 3H
4,24, q, J=7.5 Hz, 2H
5.30, s, lH (c) Production of 1,3-ovclooentanedione 2.1 g (10 mmol) Of 5-ethoxycarbonyl-3-methoxy-2-cyclopenten-1-one Na salt was placed in 20 ml of w ml of sodium hydroxide solution (4 N). It was stirred for 2.5 hours at 20° C. Then 2.6 g of hydrochloric acid (32 percent in H$_2$O) was added (pH 3). The solution was stirred for 2 hours at 90° C. and then concentrated by evaporation in a vacuum. The residue was suspended in 10 ml of ethanol and filtered. The ethanol phase was concentrated by evaporation. 0.85 g (80 percent) of 1,3-cyclopentanedione was obtained. Melting point of the product was 145° to 147° C. Data for the compound was:

$^1$H-NMR: (DMSO, 300 MHz) δ
2.38, s, 4H
5.10, s, lH
11.5–12.5, br. s, lH

What is claimed is:

1. Process for the production of 1,3-cyclopentanedione, comprising: (a) reacting a malonic acid ester in the presence of an effective amount of a base with a 4-halo-3-alkoxy-2E-butenoic acid ester to a 5,5bis-(alkoxycarbonyl)-3-alkoxy-2E-pentenoic acid ester of the formula:

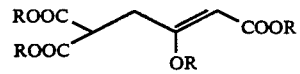

wherein the radicals R are each the same or different and are alkyl being 1 to 4 C atoms, the reaction being performed at a temperature of 0° to 180° c. and in the presence of a polar solvent, (b) cyclizing said 5,5-bis(alkoxycarbonyl)-3-alkoxy-2E-pentenoic acid ester in the presence of an effective amount of a base with the corresponding salt of 5-alkoxycarbonyl-3-alkoxy-2-cyclopenten-1-one of the formula:

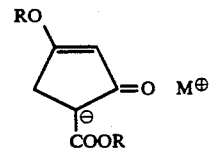

wherein M is sodium or potassium and R has the above-named meaning, the cyclization being performed at a temperature between 0° and 180° C. in the presence of a polar solvent, (c) saponifying the ester function in the presence of an effective amount of a base, the saponification being performed at a temperature of 0° to 100° C., and (d) decarboxylating the saponified compound of step (c) in the presence of an effective amount of mineral acid to the end produce, the decarboxylation being performed at a temperature of 20° to 100° C.

2. The process according to claim 1 wherein an alkali alcoholate, an alkali hyroxide or a strong organic base is used as the base in step (a).

3. The process according to claim 2 wherein step (a) is performed in the presence of a polar solvent.

4. The process according to claim 3 wherein N,N'-dimethylformamide is used as the solvent.

5. The process according to claim 3 wherein the malonic acid di-(c$_1$-C$_4$)-alkyl ester is a malonic acid di-(C$_1$-C$_2$)-alkyl ester.

6. The process according to claim 3 wherein the 4-halo-3-alkoxy-2E-butenoic acid-(C$_1$-C$_4$)-alkyl ester is a 4-chloro-3(C$_1$-C$_2$)-alkoxy-2E-butenoic acid-(C$_1$-C$_2$)-alkyl ester.

7. The process according to claim 1 wherein an alkali alcoholate or an alkali hydroxide is used as the base for the ring closure.

8. The process according to claim 7 wherein the ring closure is conducted in the presence of a polar solvent.

9. The process according to claim 8 wherein the base is an alkali alcoholate and alcohol corresponding to the alcoholate is used as a solvent.

10. The process according to claim 1 wherein an aqueous solution of an alkali hydroxide is sued as the base for step (c).

11. The process according to claim 1 wherein the decarboxylation in step (d) takes place with an aqueous solution of a mineral acid.

12. The process according to claim 11 wherein steps (a) (b), (c) and (d) are performed without isolation of the involved intermediate products.

13. The process according to claim 1 wherein step (a) is performed in the presence of a polar solvent.

14. The process according to claim 13 wherein N,N'-dimethylformamide is used as the solvent.

15. The process according to claim 1 wherein steps (a), (b), (d and (d) are performed without isolation of the involved intermediate products.

* * * * *